(12) United States Patent
Hong et al.

(10) Patent No.: US 9,402,575 B2
(45) Date of Patent: Aug. 2, 2016

(54) SAFETY BLOOD LANCET DEVICE

(71) Applicant: GMMC INC., Seoul (KR)

(72) Inventors: Kwan Ho Hong, Gyeonggi-do (KR); Kyoung Man Cho, Seoul (KR)

(73) Assignee: GMMC INC., Seoul (KR)

( * ) Notice: Subject to any disclaimer, the term of this patent is extended or adjusted under 35 U.S.C. 154(b) by 189 days.

(21) Appl. No.: 14/102,668

(22) Filed: Dec. 11, 2013

(65) Prior Publication Data

US 2015/0005670 A1 Jan. 1, 2015

(30) Foreign Application Priority Data

Jun. 25, 2013 (KR) .......................... 10-2013-0072795

(51) Int. Cl.
*A61B 5/151* (2006.01)
*A61B 5/15* (2006.01)

(52) U.S. Cl.
CPC ............ *A61B 5/15117* (2013.01); *A61B 5/1411* (2013.01); *A61B 5/150022* (2013.01); *A61B 5/15113* (2013.01); *A61B 5/150183* (2013.01); *A61B 5/15194* (2013.01); *A61B 5/150412* (2013.01); *A61B 5/150503* (2013.01); *A61B 5/150824* (2013.01)

(58) Field of Classification Search
CPC .......... A61B 5/15186–5/15198; A61B 5/1411; A61B 5/150022; A61B 5/151; A61B 5/15101; A61B 5/15113; A61B 5/15117; A61B 5/15126–5/15132; A61B 5/150534; A61B 5/15058; A61B 1/150564; A61B 5/150587; A61B 5/150595; A61B 5/150625; A61B 1/150633; A61B 1/150641
See application file for complete search history.

(56) References Cited

U.S. PATENT DOCUMENTS

| | | | |
|---|---|---|---|
| 4,517,978 A | 5/1985 | Levin et al. | |
| 5,613,978 A | 3/1997 | Harding | |
| 5,964,718 A * | 10/1999 | Duchon | A61B 5/1411 600/583 |
| 2009/0281458 A1* | 11/2009 | Faulkner | A61B 5/15186 600/583 |
| 2011/0313439 A1* | 12/2011 | Ishikura | A61B 5/1411 606/182 |

FOREIGN PATENT DOCUMENTS

| | | |
|---|---|---|
| JP | 10-508527 A | 8/1998 |
| KR | 10-2006-0052317 A | 5/2006 |
| KR | 10-0820523 B1 | 4/2008 |
| KR | 10-0923778 B1 | 10/2009 |
| KR | 10-0932946 B1 | 12/2009 |

OTHER PUBLICATIONS

Korean Office Action issued in counterpart foreign patent application on May 13, 2014.*

* cited by examiner

*Primary Examiner* — Devin Henson
*Assistant Examiner* — David J McCrosky
(74) *Attorney, Agent, or Firm* — Rabin & Berdo, P.C.

(57) ABSTRACT

A safety blood lancet device includes an outer sleeve. A fixing tube fixed in the outer sleeve has a cantilever hook. A carrier is elastically inserted into the fixing tube, and in which a lancet is separably installed at a front end thereof, a rear tip which is at a rear end of the outer sleeve and connected with a rear end of the carrier so as to load the carrier by pulling the carrier toward a rear side. A female nut is separably coupled to the outer sleeve. A front tip is rotatably installed at a front end of the female nut and in which a needle of the lancet protrudes through a front end thereof when the carrier is shot. A rear end of the fixing tube is selectively inserted into a safety cap and is elastically installed toward a front side of the outer sleeve.

6 Claims, 9 Drawing Sheets

SAFETY BLOOD LANCET DEVICE

BACKGROUND OF THE INVENTION

1. Field of the Invention

The present invention relates to a blood lancet device which collects a small amount of blood from a human body, and more particularly, to a safety blood lancet device in which a loading operation in an exposed state of a lancet is not allowed, and a loading state of the lancet can be visually checked from the outside, and also it is possible to previously prevent damage of components due to applying of excessive force, when adjusting a penetration depth of a needle of a lancet.

2. Description of the Related Art

A Blood lancet device is primarily used by diabetic patients who are required to regularly check their blood sugar levels, but it is also used in various other fields where the collection of blood samples is required.

The blood lancet device is configured so that a lancet including a body and a needle fixed to the body is inserted therein and the needle penetrates the skin to a predetermined depth by applied elastic force. For example, the blood lancet device is disclosed in Korean Patent No. 10-0820523 and U.S. Pat. No. 4,517,978. In case of these patents, if a button is pressed after the lancet is inserted and a sleeve is pulled back, the lancet is shot forward, and the needle penetrates the skin and is then withdrawn in a flash.

In the general blood lancet device having the above-mentioned configuration, which was sold in the market, a penetration depth of the needle was uniformly fixed. However, since people's skin may have different thicknesses, and also the collection of blood may be performed at different parts of the body, it was necessary to adjust the penetration depth of the needle to the skin.

Therefore, a blood lancet device that could adjust the depth of penetration was developed. Korean Patent No. 10-0820523 and U.S. Pat. No. 5,613,978 show structures of the blood lancet device in detail. In these patents, a user can adjust the penetration depth of the needle to the skin by turning a control tip.

However, in the conventional blood lancet device, since loading and shooting operations may be performed even in an exposed state of a lancet, the lancet may be shot due to user's carelessness, and thus a user and other persons may be injured. Also, it is not possible to check whether the lancet is loaded in an unexposed state of the lancet after loading the lancet.

Also, in the conventional blood lance device, when a user rotates the control tip in order to adjust the penetration depth of the lancet, components of the device may be damaged or separated from each other if excessive force is applied to the control tip, and also patients who will have blood taken may feel psychological fear due to impact sound generated between the components when loading the lancet.

Also, in the conventional blood lance device, since an ultrasonic welding method is employed to manufacture rigid products when assembling the components, it is necessary to prepare separate equipment for ultrasonic welding, and also it is difficult to perform the assembling process while satisfying ultrasonic welding conditions.

SUMMARY OF THE INVENTION

An object of the present invention is to provide a safety blood lancet device in which loading and shooting operations are not allowed in an exposed state of a lancet.

Another object of the present invention is to provide a safety blood lancet device which is capable of easily visually checking whether a lancet is loaded in an unexposed state of the lancet after loading the lancet through a window.

A further object of the present invention is to provide a safety blood lancet device which is capable of previously preventing damage of components by restricting a rotating angle of a control tip controlling a penetration depth of a needle of a lancet.

A yet further object of the present invention is to provide a safety blood lancet device which is capable of absorbing impact sound generated between the components when loading the lancet, thereby preventing patients who will have blood taken from feeing psychological fear due to the impact sound.

A yet further object of the present invention is to provide a safety blood lancet device which is capable of maintaining a rigidly assembled state without ultrasonic welding.

According to an aspect of the present invention, there is provided a safety blood lancet device including: an outer sleeve; a fixing tube which is fixed in the outer sleeve and has a cantilever hook extended from a rear end thereof; a carrier which is elastically inserted into the fixing tube to be moved forward and backward, and in which a lancet is separably installed at a front end thereof; a rear tip which is installed at a rear end of the outer sleeve and connected with a rear end of the carrier so as to load the carrier by pulling the carrier toward a rear side; a female nut which is separably coupled to a front end of the outer sleeve, a front tip which is rotatably installed at a front end of the female nut and in which a needle of the lancet protrudes through a front end thereof when the carrier is shot; and a safety cap in which a rear end of the fixing tube is selectively inserted and which is elastically installed toward a front side of the outer sleeve in the outer sleeve, wherein, when the female nut is separated from the fixing tube, the safety cap presses the cantilever hook of the fixing tube toward the carrier and catches a part of the carrier, thereby preventing the carrier from being moved in a loading direction.

A front portion of the carrier may have a plurality of guide ribs which is coupled in the fixing tube to be slid forward and backward, and a rear portion of the carrier may have a cross rib which is coupled in the inner sleeve coupled in the outer sleeve to be slid forward and backward.

The safety blood lancet device may further include a window which is fitted to a window coupling hole of the outer sleeve and a window coupling hole of the fixing tube at the same time.

A color may be applied to one of the plurality of guide ribs of the carrier, which corresponds to the window, so as to check a loading state of the carrier through the window.

A pair of first inclined ribs may be defined at an angle of 180° at a rear end of a inner tip fixed in the front tip, and a pair of second inclined ribs which comes in contact with the pair of first inclined ribs may be defined at a part of the female nut, and, when the female nut is rotated in one direction, the pair of first inclined ribs of the inner tip may be slid up along the pair of second inclined ribs of the female nut, and thus the front tip may protrude to a front side, and when the inner tip is rotated in a reverse direction, the front tip may be moved backward.

When the inner tip is returned to its original position, ends of the inclined ribs of the inner tip and the female nut may be alternately engaged with each other, and thus rotation of the inner tip may not be stopped.

A noise preventing rubber ring may be coupled to a front end of the inner sleeve, and thus it is possible to minimize noise generated when the carrier is loaded.

The safety blood lancet device may further include an ejector of which a part is exposed to an outside of the outer sleeve and the rest part is slidably coupled in the carrier so as to press the lancet and thus separate the lancet from the carrier.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts.

Figure 1:
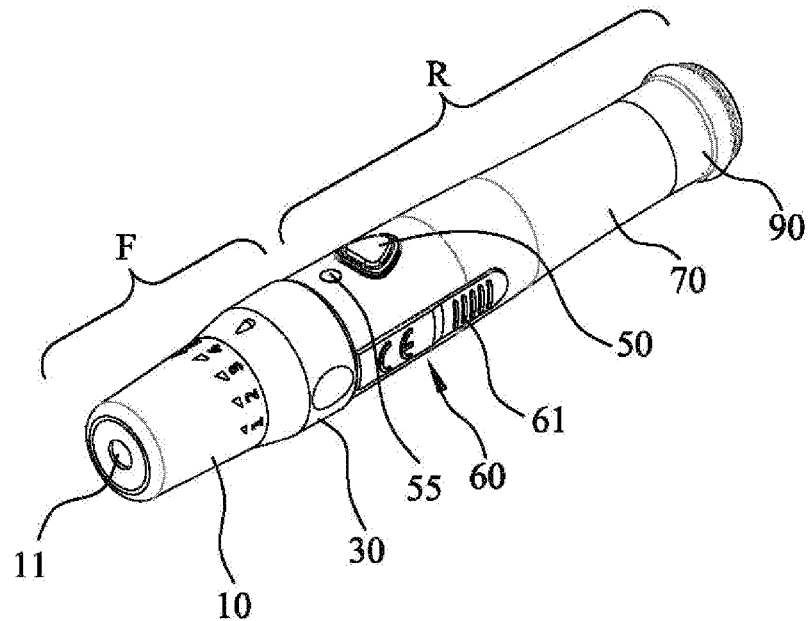
FIG. 1 is a perspective view of a safety blood lancet device in accordance with one embodiment of the present invention.
Figure 2:
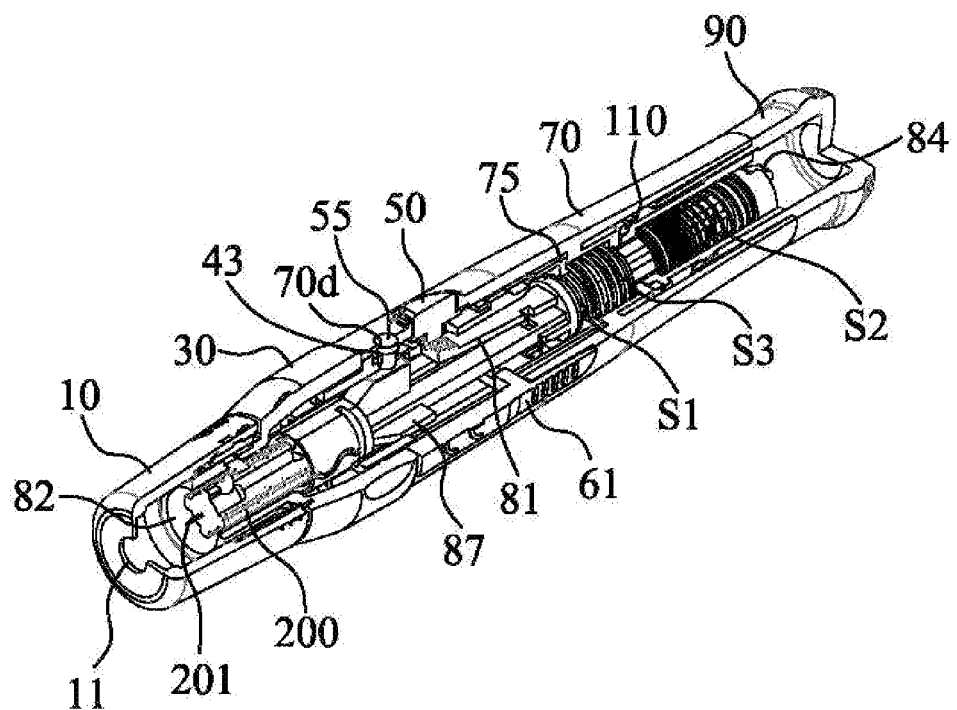
FIG. 2 is a perspective view of the safety blood lancet device partially cut away in accordance with one embodiment of the present invention.
Figure 3:
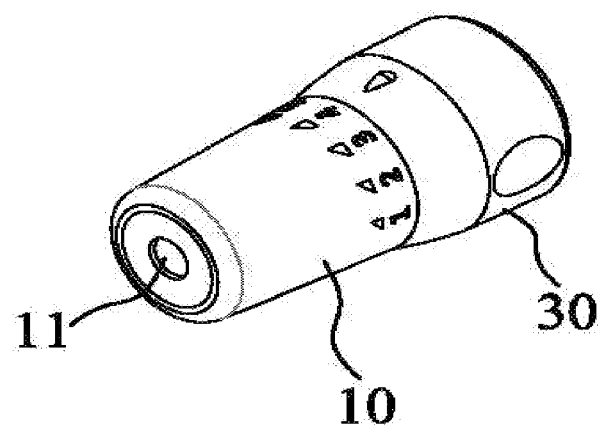
FIG. 3 is an assembled perspective view of a front unit illustrated in FIG. 1.
Figure 6:
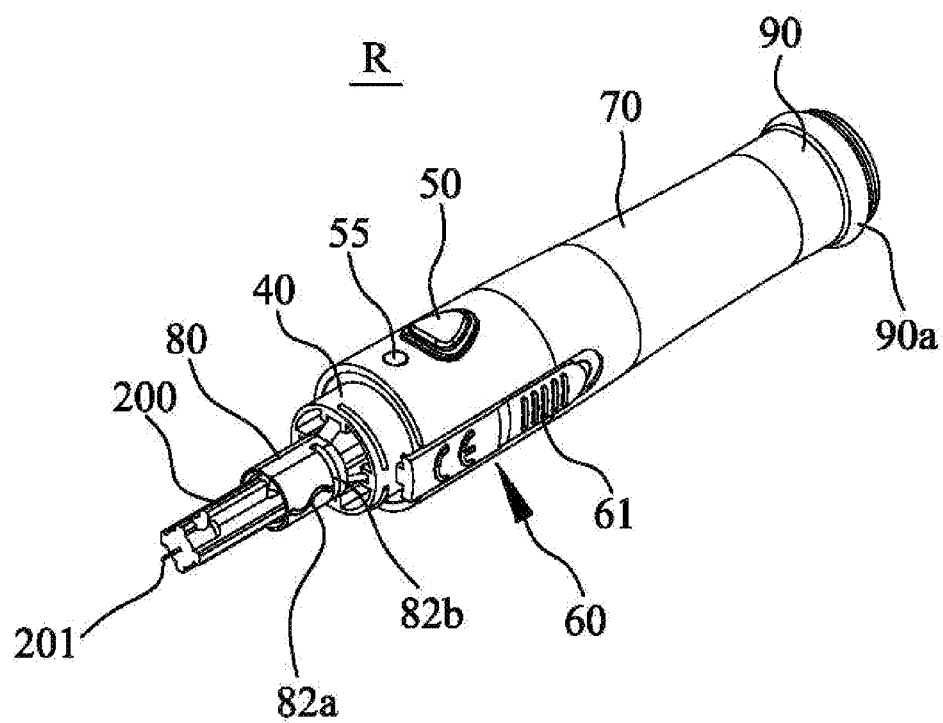
FIG. 6 is an assembled perspective view of a rear unit illustrated in FIG. 1.

Referring to FIGS. 1 and 2, a safety blood lancet device 1 in accordance with one embodiment of the present invention includes a front unit F (referring to FIG. 1), a rear unit R (referring to FIG. 6) which is separably coupled to the front unit F, and a lancet 200.

First of all, a configuration of the front unit F will be described with reference to FIGS. 3 to 5B. The front unit F includes a front tip 10, an inner tip 20 and a female nut 30.

The inner tip 20 is disposed in the front tip 10, and a pair of rail grooves 10a and 10b is provided in both sides of an internal surface of the front tip 20 so that the inner tip 20 is coupled with the front tip 20. The inner tip 20 has a pair of rail hooks 20a and 20b provided at both sides of an outer surface thereof to be coupled to the pair of rail grooves 10a and 10b.

Further, a front end of the female nut 30 is inserted into the inner tip 20. To this end, the inner tip 20 has a pair of inner protrusions 21 and 22 provided on an inner surface thereof. The female nut 30 has coupling grooves 30a and 30b provided in an outer surface of a front end thereof so as to be coupled with the inner protrusions 21 and 22 of the inner tip 20.

Since the front tip 10 is coupled with the inner tip 20, and the inner tip 20 is coupled with the front end of the female nut 30, they may be regarded as the front unit F which is a single unit. The front unit F is repeatedly coupled to and separated from the rear unit R in order to insert the lance 200, which is a disposable part, into a holder portion of a carrier 80.

The front unit F may adjust a penetration depth of a needle 201 protruding in a predetermined length from a front end of the lancet 200. Hereinafter, a structure of adjusting the penetration depth of the needle 201 of the lancet 201 will be described in detail.

Referring to FIG. 2, a rear end of the female nut 30 is rotated by about a half turn and assembled to a fixing tube 40, and the front end thereof has a stepped portion having a smaller outer diameter than that of the front end. Further, the front end of the female nut 30 has a spiral groove 30a (referring to FIG. 5C) defined over an angle of approximately 180° and seven positioning grooves 30b defined at angular intervals of about 25° along an outer circumference thereof in an axial direction.

The inner protrusions 21 and 22 defined on the inner surface of the inner tip 20 are inserted and assembled into the spiral groove 30a and the positioning grooves 30b. The inner tip 20 has the pair of straight rail hooks 20a and 20b provided on the outer surface thereof in the axial direction, and the inner protrusions 21 and 22 provided on the inner surface thereof. In this case, as the rail hooks 20a and 20b are snap-coupled to the rail grooves 10a and 10b of the front tip 10, the front tip 10 and the inner tip 20 are rotated together. At this time, one of the inner protrusions 21 and 22 defined on the inner surface of the inner tip 20 is inserted into the spiral groove 30a, and the other is inserted into the positioning groove 30b to set a position of the front tip 10.

Also, the inner tip 20 is assembled with the front tip 10 in a fitting manner, and thus the inner tip 20 has two cut-away portions 20C defined at an angle of 180° in the axial direction to be smoothly rotated.

In a state in which the front unit F as described above is assembled to the rear unit R, if the front tip 10 is rotated in one direction or reverse in order to adjust the penetration depth of the needle, the front tip 10 is rotated together with the inner tip 20. Therefore, the inner protrusions 21 and 22 of the inner tip 20 are rotated along the spiral groove 30a of the female nut 30 to be moved forward or backward, and thus a distance between a front end 11 of the front tip 10 and the lancet 200 is adjusted to be increased or decreased.

Figure 4:
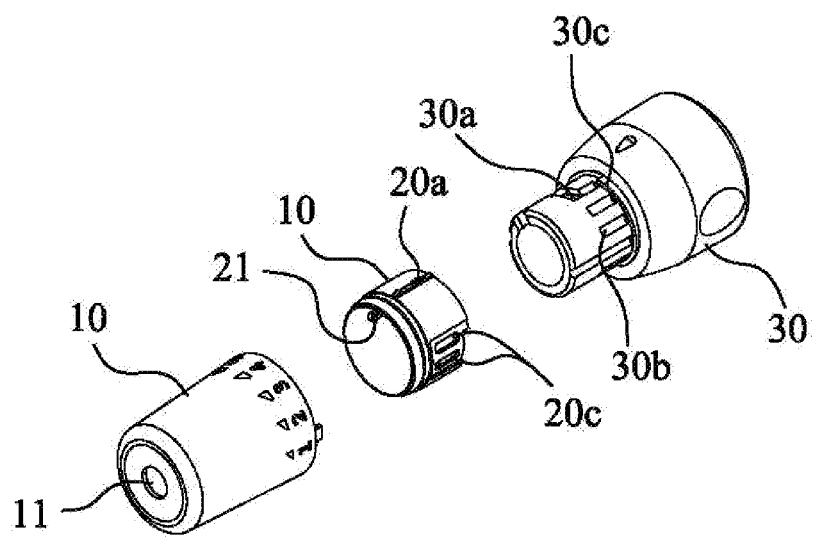
FIG. 4 is an exploded perspective view of the front unit illustrated in FIG. 3.
Figure 5A:
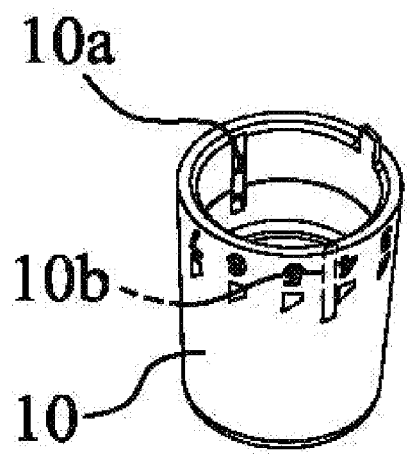
FIG. 5A is a perspective view of a front tip illustrated in FIG. 4.
Figure 5B:
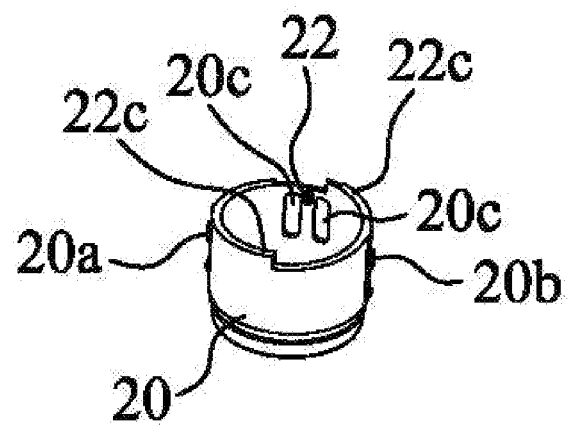
FIG. 5B is a perspective view of an inner tip illustrated in FIG. 4.
Figure 5C:
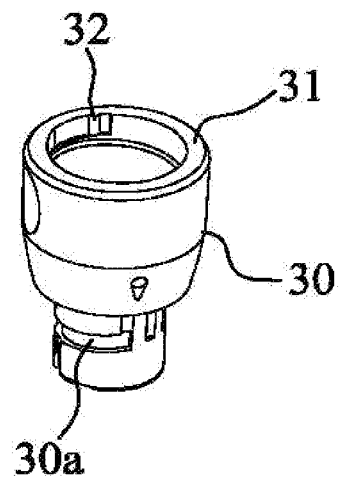
FIG. 5C is a perspective view of a female nut illustrated in FIG. 4.

Further, as illustrated in FIGS. 4, 5A and 5B, a rear end of the inner tip 20 has a pair of first inclined ribs 22c defined at an angle of 180°. Also the female nut 30 has a pair of second inclined ribs 30c defined at a contacting portion with the first inclined ribs 22c upon coupling the inner tip 20 with the female nut 30 so as to correspond to the pair of first inclined ribs 22c.

In this case, one of the pair of first inclined ribs 22c is longer than the other thereof. Therefore, if the female nut 30 is rotated in one direction, the pair of first inclined ribs 22c of the inner tip 20 is slid up along the pair of second inclined ribs 30c of the female nut 30, and the front tip 10 protrudes to a front side. If the inner tip 20 is rotated in a reverse direction, the pair of first inclined ribs 22c is slid down along the pair of second inclined ribs 30c, and thus the front tip 10 is moved backward.

Meanwhile, when the inner tip 20 is returned to its original position, ends of the inclined ribs 22c and 30c of the inner tip 20 and the female nut 30 are alternately engaged with each other, and thus the inner tip 20 may not be rotated any more. Therefore, even though a user rotates the inner tip 20 a little harder to cross the original position, the inner tip 20 is prevented from being rotated, and thus components of the front unit F are prevented from being damaged or disassembled.

Further, the front tip 10 is inserted into the inner tip 20 and rotated together, and thus a penetration degree of the front tip 10 is adjusted. Here, since the inclined ribs 22c and 30c is linearly in contact with each other, the front tip 10 is prevented from being randomly pressed, and thus it is possible to precisely adjust the penetration depth.

A configuration of the rear unit R will be described in detail with reference to FIGS. 6 to 10B. The rear unit R includes the fixing tube 40, a button 50, an ejector 60, an outer sleeve 70, a safety cap 75, a carrier 80, a rear tip 90 and an inner sleeve 95.

The fixing tube 40 has a hole defined therein, through which the carrier 80 passes. The female nut 30 is coupled to a front end of the fixing tube 40 in a screwing manner, and the safety cap 75 is coupled to a rear end thereof.

The fixing tube 40 has a cut-away portion 41 which is defined along one side thereof and through which a part of the ejector 60 passes and moves, and a cantilever hook 42 which is defined at the other side thereof to catch a flange 83 of the carrier 80 for safety when the needle 201 of the lancet 200 is exposed, thereby preventing the lancet 200 from being shot.

Further, the fixing tube 40 includes a window coupling hole 43 in which a window 55 is inserted and fixed, a protrusion rib 45 on which the safety cap 75 is inserted to guide a rectilinear movement of the safety cap 75, a finger hole 44 in which a finger 81 of the carrier 80 is inserted, and a finger latching portion 44a. The button 50 is operably disposed in the finger hole 44, and a guide rib 46 is provided at an opposite portion to the button 50, such that the safety cap 75 is inserted thereon and linearly moved forward and backward.

Figure 9:
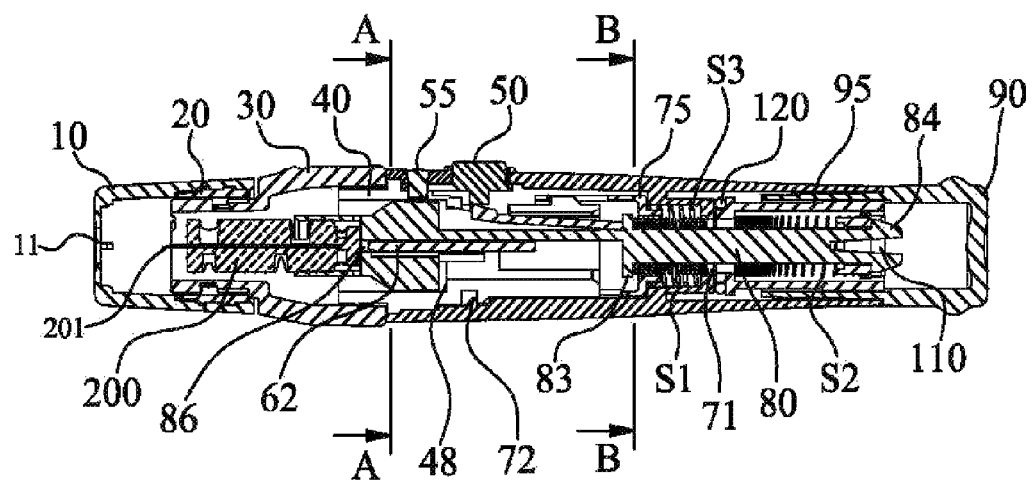
FIG. 9 is a cross-sectional view of the safety blood lancet device illustrated in FIG. 1.
Figure 10A:
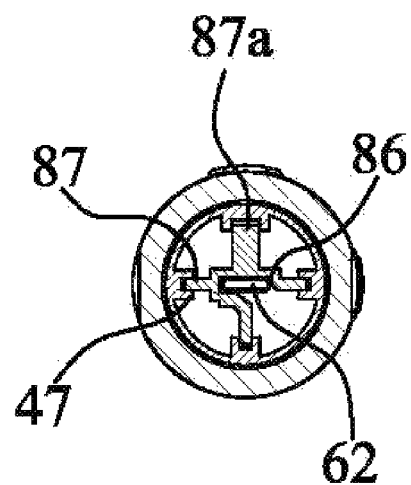
FIG. 10A is a cross-sectional view taken along a line A-A of FIG. 9.
Figure 10B:
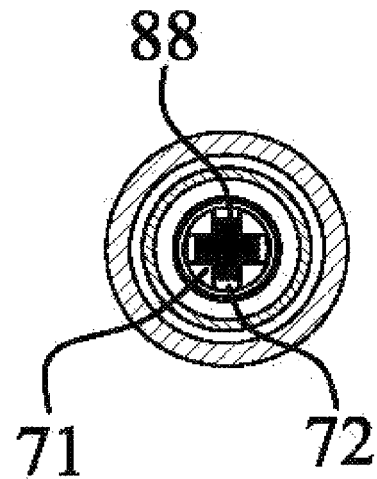
FIG. 10B is a cross-sectional view taken along a line B-B of FIG. 9.

As illustrated in FIG. 9, the outer sleeve 70 is assembled to an outer surface of the fixing tube 40. At this time, an inner hook 72 of the outer sleeve 70 is coupled with a fixing portion 49 of the fixing tube 40, and a cylindrical window 55 is fitted and fixed into a window coupling hole 70d of the outer sleeve 70 and the window coupling hole 43 of the fixing tube 40 from an outside of the outer sleeve 70. Therefore, the present invention may maintain a rigidly assembled state of components without a conventional ultrasonic welding operation.

Meanwhile, a stepped portion 48 is provided at a distal end of a rail groove of the fixing tube 40 so that the carrier 80 is stopped by the stepped portion 48 when being moved backward in a predetermined distance. Thus, when pulling back the rear tip 90 in order to load the carrier 80, a user is prevented from pulling back unlimitedly it, and thus it is possible to prevent the rear tip 90 from being damaged.

The button 50 is disposed at a position corresponding to the finger hole 44 so as to shoot the loaded lancet 200.

The button 50 is inserted and coupled into the outer sleeve 70 so that a pair of fixing protrusions 50a and 50b of the button 50 correspond to a pair of fixing grooves 74a and 74b of the outer sleeve 70. In this case, a stepped flange 70c is defined at an edge portion of a button hole 70b so that the carrier 80 may be shot only when a user recognizes a fact that the button 50 is pressed, whereby it is possible to prevent the button 50 to be pressed easily or prevent occurrence of malfunction.

The ejector 60 may be disposed at an angle of about 90° with respect to the button 50 or the window 55 installed on the outer sleeve 70 in order to allow a user to operate the ejector 60 with a thumb of a hand gripping the safety blood lance device 1.

The ejector 60 includes a handle part 61 exposed to an outside of the outer sleeve 70, and a pressing portion 62 extended from one side of the handle portion 61. The pressing portion 62 is moved together with the handle portion 61 when the handle portion 61 is moved in an axial direction of the safety blood lance device 1.

Meanwhile, in order to replace the lancet 200 used, the female nut 30 screwed to the fixing tube 40 is separated from the fixing tube 40 so that the lancet 200 is exposed, and then, as described above, the handle portion 61 is pushed toward a front side of the safety blood lance device 1, and thus the pressing portion 62 passes through a through-portion 86 of the carrier 80 and pushes the lancet 200 out so that the lancet 200 is separated from the carrier 80.

Also, the ejector 60 has rail grooves 60b defined at both sides thereof, and rails 70a of the outer sleeve 70 are inserted into the rail grooves 60b of the ejector 60. Therefore, a rear portion of the ejector 60 is prevented from being severely pressed and broken.

In addition, the ejector 60 has a plurality of protrusions 65 provided at both sides thereof. Therefore, when the elector 60 is pushed, the protrusions 65 of the ejector 60 are interfered with protrusions 70e provided at ends of both rails of the outer sleeve 70, and thus a user may recognize that the ejector 60 is operated (moved).

Front and rear sides of the outer sleeve 70 are opened, and a partition rib 71 is provided at a center thereof. The partition rib 71 has a cross hole 72, and a third spring S3, the safety cap 75, the fixing tube 40 and the carrier 80 are received in a front side of the outer sleeve 70 based on the partition rib 71. Further, the outer sleeve 70 has cut-away portions defined in an outer surface thereof to receive the button 50, the window 55 and the ejector 60.

The safety cap 75 has a cylindrical shape covering the fixing tube 40 and a guide rib 76 provided therein. The guide rib 76 serves to bend the cantilever hook 42 of the fixing tube 40, which catches the flange 83 of the carrier 80 for safety when the needle 201 of the lancet 200 is exposed and thus prevents the lancet 200 from being shot, toward the flange 83.

Further, the safety cap 75 has a guide hole 77 which is moved backward upon loading the carrier 80 to engage with and catch the cantilever hook 42 of the fixing tube 40, a coupling hole 45 which is coupled with the protrusion rib 45 of the fixing tube 40, and an opening 79 which is coupled with the guide rib 46 of the fixing tube 40. A rear side of the safety cap 75 has a cylindrical shape in which the third spring S3 is fixed.

The carrier 80 includes the finger 81, a holder portion, the flange 83, a hook portion 84, the rectangular through-portion 86, a plurality of guide ribs 87 and a cross rib 88.

In order for the finger 81 to be snap-coupled to the finger latching portion 44a of the fixing tube 40, one end of the finger 81 is fixed to the carrier 80, and the other end thereof is disposed toward an outside of the carrier 80, and thus the finger 81 may be elastically coupled to the finger latching portion 44a.

Figure 7:
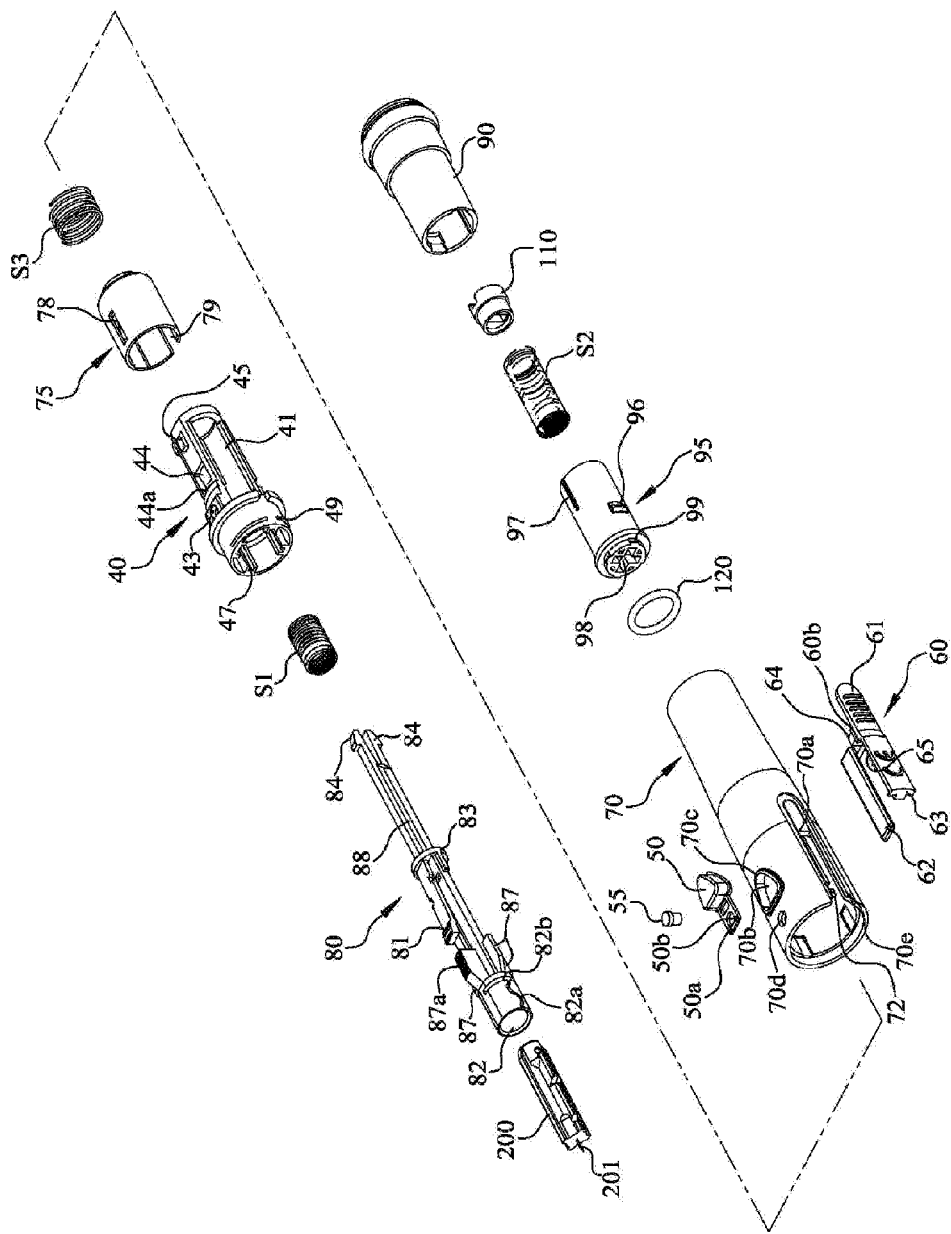
FIG. 7 is an exploded perspective view of the rear unit illustrated in FIG. 6.
Figure 8A:
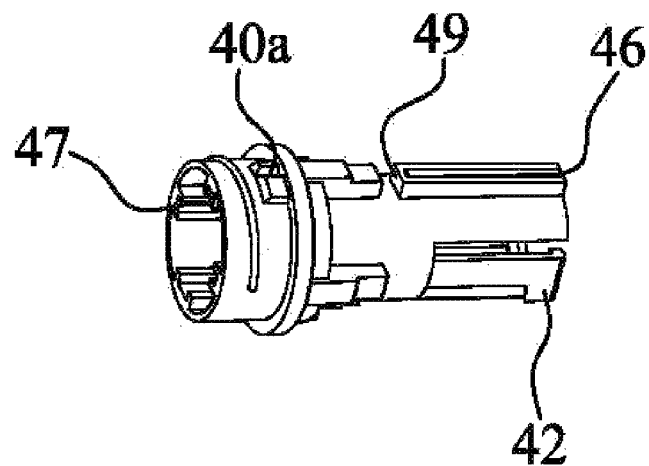
FIG. 8A is a perspective view of a fixing tube illustrated in FIG. 7.
Figure 8B:
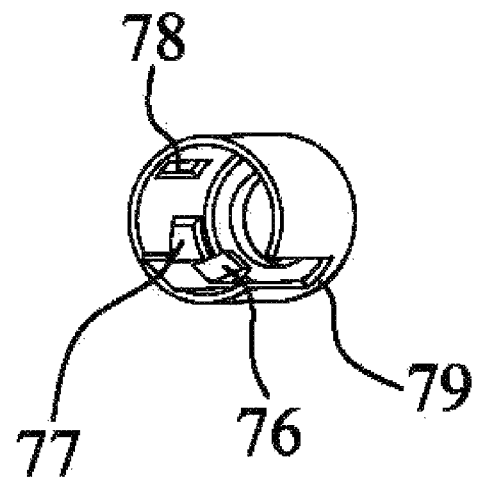
FIG. 8B is a perspective view of a safety cap illustrated in FIG. 7.
Figure 8C:
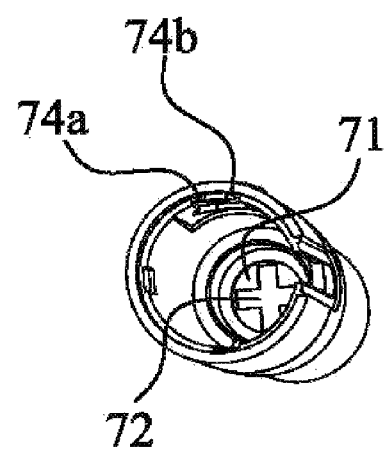
FIG. 8C is a perspective view of an outer sleeve illustrated in FIG. 7.

The holder portion 82 is defined at a front end of the carrier 80 so that the lancet 200 is separably coupled thereto. The holder portion 82 has a cylindrical shape which may smoothly couple and separate the lancet 200, and a side cut-away portion 82a straightly defined at a side surface thereof. In this case, in order to prevent an error in which, when the lancet 200 is inserted into the holder portion 82, the lancet 200 is slantly inserted into a split gap of the side cut-away portion 82a, and thus the needle 201 of the lancet 200 of the front tip 10 may not pass through a hole of the front end 11, the side cut-away portion 82a of the holder portion 82 has a zigzag as illustrated in FIG. 7 so that the lancet 200 is coaxially inserted into the holder portion 82 when inserting the lancet 200 into the holder portion 82, thereby preventing the error.

The flange 83 is provided at an approximately middle portion of the carrier 80 and passes through the fixing tube 40 so as to be moved forward and backward in the fixing tube 40. The flange 83 elastically supports one end of a first spring S1. The first spring S1 is disposed between the flange 83 of the carrier 80 and the partition rib 71 of the outer sleeve 70. Therefore, when the carrier 80 is moved backward, the first spring S1 is compressed and then released by an operation of the button 50, thereby shooting the carrier 80 forward.

The hook portion 84 is provided at a rear side of the carrier 80 and hooked to an end ring 110 assembled to the inner sleeve 95, which will be described later. Thus, if the rear tip 90 is pulled back toward a rear side of the safety blood lancet device 1, the carrier 80 moved together with the rear tip 90 is also moved backward and thus loaded.

The rectangular through-portion 86 is provided at a center of the carrier 80 so as to guide the pressing portion 62 of the ejector 60 to be passed and moved therethrough.

The plurality of guide ribs 87 has a roughly cross shape and is inserted into four guide rail grooves 47 defined in the fixing tube 40 in order to maintain straightness upon shooting the carrier 80.

Meanwhile, a predetermined color is applied to a surface of one 87a of the plurality of guide ribs 87 so that the color is not displayed through the window 55 when the carrier 80 is moved forward, i.e., in an unloaded state of the carrier 80, and the guide rib 87a having the color is displayed through the window 55 when the carrier 80 is moved backward, i.e., in a loaded state of the carrier 80, and thus a user may easily grasp whether the carrier 80 is loaded by the color displayed through the window 55.

The cross rib 88 is provided at a rear side of the plurality of guide ribs 87 and inserted into the cross hole 72 defined in the partition rib 71 of the outer sleeve 70. The cross rib 88 serves to guide the carrier 80 in cooperation with the plurality of guide ribs 87 to be straightly movable, when the carrier 80 is shot.

Therefore, when the carrier 80 is moved forward and backward, the carrier 80 shot by elastic force of the first spring S1 is precisely guided to be linearly moved by the plurality of guide ribs 87 of the carrier 80 and the plurality of rail groove 47 of the fixing tube 40, and thus it is possible to prevent a limitation occurred when a conventional blood lancet device is used, in which the lancet 200 pierces the skin.

The rear tip 90 is coupled and fixed to the inner sleeve 95 to be operated together with the inner sleeve 95. The rear tip 90 serves to pull the carrier 80 toward a rear side of the safety blood lancet device 1 and thus load the carrier 80. When the rear tip 90 is pulled back, the finger 81 of the carrier 80 is still latched to the button 50 and the first spring S1 is compressed. In this situation, if the button 50 is pressed, the finger 81 of the carrier 80 is separated from the finger hole 44 of the fixing tube 40, and the carrier 80 is moved forward together with the lancet 200 in a flash by the elastic force of the first spring S1. Therefore, the needle 201 of the lancet 200 passes through the a needle passing-through hole 11a of the front tip 10 and penetrates the skin, whereby a small amount of blood may be discharged to an outside of the skin.

The inner sleeve 95 has a diameter which is smaller than the outer sleeve 70, and thus the inner sleeve 95 may be inserted into a rear end of the partition rib 71 of the outer sleeve 70.

The inner sleeve 95 has a hook protrusion 96 defined at an outer surface thereof to be coupled with the rear tip 90 and a guide protrusion rib 97 defined at the outer surface thereof. Therefore, the inner sleeve 95 is coupled and fixed to the rear tip 90 which pulls the carrier 80 toward the rear side of the safety blood lancet device 1 in order to load it.

Further, an end ring 110 to which the hook portion 84 defined at the rear end of the carrier 80 is latched is coupled in the inner sleeve 95. The end ring 110 has a stepped portion, and the second spring S2 is disposed between the stepped portion of the end ring 100 and the front end of the inner sleeve 95. The second spring S2 serves to absorb a shock generated by hitting of the lancet 200 and reinstate the lancet 200 slightly to a rear side.

Furthermore, a noise preventing rubber ring 120 is provided at a front end 99 of the inner sleeve 95 so as to restrain noise generated among components when the carrier 80 is loaded and thus resolve patients' sensation of fear due to the noise.

Furthermore, a cross hole 98a through which the cross rib 88 of the carrier 80 passes is defined in a front through-portion 98 of the inner sleeve 95. Therefore, since the carrier 80 is guided by the cross hole 72 of the outer sleeve 70 and the cross hole 98a of the inner sleeve 95, through which the cross rib 88 passes, the rear side of the carrier 80 is prevented from shaking when the carrier 80 is linearly moved, thereby securing reliable feature of straight of the carrier 80.

Figure 11:
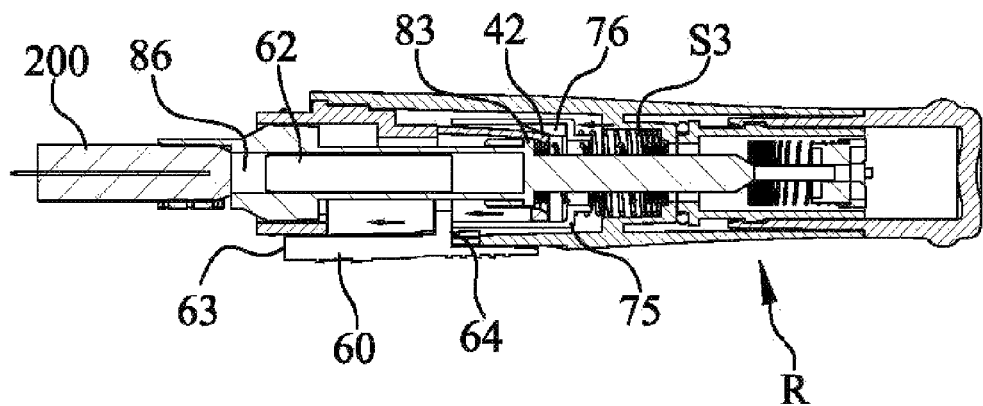
FIG. 11 is a cross-sectional view of the safety blood lancet device illustrated in FIG. 6.

Meanwhile, in the safety blood lancet device 100, as illustrated in FIG. 11, the loading operation may not be performed, even though the lancet 200 is fitted to the holder portion 82 of the carrier 80 while the front unit F is separated, and the rear tip 90 is then pulled toward the rear side of the safety blood lancet device 100. In this state, since the cantilever hook 42 of the fixing tube 40 is pressed by the guide rib 76 of the safety cap 75, and thus the flange 83 is caught by the cantilever hook 42, the carrier 80 may not be moved in a loading direction.

Figure 12:
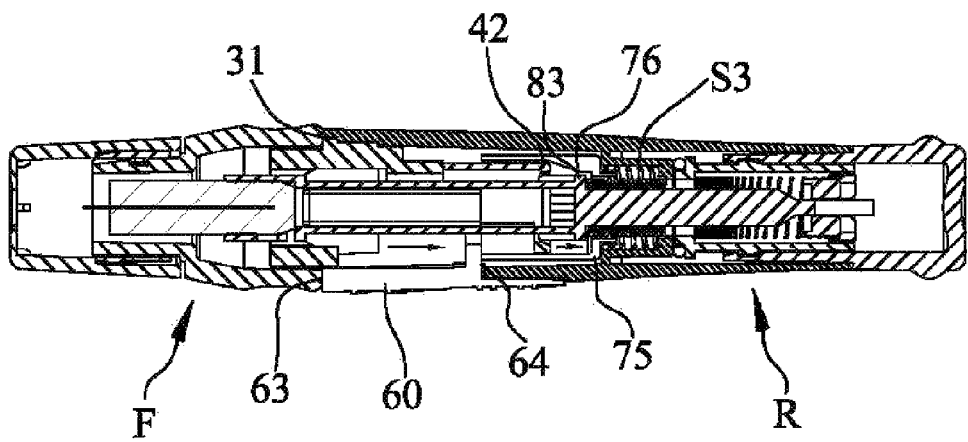
FIG. 12 is a cross-sectional view illustrating a state in which the front unit is assembled to the safety blood lancet device illustrated in FIG. 11.

However, as illustrated in FIG. 12, if the front unit F is installed at the rear unit R, a rear side surface 31 of the female nut 30 pushes the a front side surface 63 of the ejector 60. Therefore, the safety cap 75 disposed at a rear side surface 64 of the ejector 60 is pushed back by the ejector 60, and thus pressing force of the guide rib 76 applied to the cantilever hook 42 of the fixing tube 40 is released. Thus, the cantilever hook 42 is moved to its original position and the flange 83 of the carrier 80 caught by the cantilever hook 42 is released. Therefore, the carrier 80 may be loaded by pulling the rear tip toward 90 the rear side of the safety blood lancet device 100 and may be also shot.

In the present invention as described above, since it is impossible to load and shoot the carrier while the front unit is not coupled to the rear unit and thus the lancet is exposed to the outside, the exposed lancet is previously prevented from being shot together with the carrier, whereby a safety accident that the user is pricked by the needle of the lancet due to user's carelessness can be prevented.

Also, in the present invention, when the carrier is loaded by pulling the rear tip toward the rear side while the front unit is coupled to the rear unit, the user can easily visually check the loading state by recognizing the color displayed through the window from the outside.

Further, in the present invention, the female nut is prevented from being reversely rotated by the pair of first inclined ribs defined at an angle of 180° at the rear end of the inner tip and the pair of second inclined ribs of the female nut corresponding to the pair of first inclined ribs, and thus the components can be prevented from being damaged or separated from each other due to user's excessive force, and also the front tip can be precisely moved forward and backward.

Also, in the present invention, since the button shooting the carrier does not protrude excessively to the outside, sensitivity of the button is reduced, and thus it is possible to prevent malfunction of the button, and also since the noise generated among the components when the rear tip is pulled and then released in order to load the carrier can be minimized, the patients who will have blood taken can be prevented from feeling psychological fear.

Further, in the present invention, the ejector removing the used lancet is disposed at an angle of about 90° with respect to the button, and thus a user can easily remove the lancet from the rear unit using a thumb of a hand gripping the safety blood lance device.

Also, in the present invention, a rigidly assembled state can be maintained by just manually assembling the components without a separate ultrasonic welding operation.

It will be apparent to those skilled in the art that various modifications and variations can be made in the present invention. Thus, it is intended that the present invention covers the modifications and variations of this invention provided they come within the scope of the appended claims and their equivalents.

What is claimed is:

1. A safety blood lancet device comprising:
    an outer sleeve;
    a fixing tube fixed in the outer sleeve and including
        a cantilever hook extended from a middle portion to a rear end of the fixing tube, and
        guide rail grooves formed on an inner surface of a front side of the fixing tube;
    a safety cap disposed inside the outer sleeve, into which a rear end portion of the fixing tube is selectively inserted;
    a carrier elastically inserted into the fixing tube to be moved forward and backward, and including
        a holder portion formed in a front end portion of the carrier and having a cylindrical shape, the holder portion receiving a lancet,
        guide ribs protruding in a radial manner from an outer surface of the carrier, the guide ribs being inserted into the guide rail grooves formed in the fixing tube, and
        a cross rib axially extending from a rear end of the carrier and having a hook portion formed at a rear end of the cross rib;
    an inner sleeve inserted into a rear end portion of the outer sleeve, through which the cross rib of the carrier passes;
    an end ring coupled with the inner sleeve at a rear end of the inner sleeve, to which the hook portion of the carrier is hooked;
    a rear tip having a cylindrical shape and, a front portion of the rear tip being inserted into the rear end of the outer sleeve such that an outer surface of the rear tip contacts with an inner surface of the outer sleeve and an inner surface of the rear tip contacts with an outer surface of the inner sleeve, a rear portion of the rear tip being disposed outside the outer sleeve, the rear tip being connected with a rear end of the hook portion so as to load the carrier by pulling the carrier toward a rear side;
    a female nut which is separably coupled to a front end of the outer sleeve; and
    a front tip which is rotatably installed at a front end of the female nut and in which a needle of the lancet protrudes through a front end thereof when the carrier is shot,
    wherein, when the female nut is separated from the fixing tube, the safety cap presses the cantilever hook of the fixing tube toward the carrier and catches a part of the carrier, thereby preventing the carrier from being moved in a loading direction.

2. The device of claim 1, further comprising a window which is fitted to a window coupling hole of the outer sleeve and a window coupling hole of the fixing tube at the same time.

3. The device of claim 2, wherein a color is applied to one of the guide ribs of the carrier, which corresponds to the window, so as to check a loading state of the carrier through the window.

4. The device of claim 1, wherein a pair of first inclined ribs is defined at an angle of 180° at a rear end of an inner tip fixed in the front tip, and
    a pair of second inclined ribs which comes in contact with the pair of first inclined ribs is defined at a part of the female nut, and
    when the female nut is rotated in one direction, the pair of first inclined ribs of the inner tip is slid up along the pair of second inclined ribs of the female nut, and thus the front tip protrudes to a front side, and when the inner tip is rotated in a reverse direction, the front tip is moved backward.

5. The device of claim 1, wherein a noise preventing rubber ring is coupled to a front end of the inner sleeve.

6. The device of claim 1, further comprising an ejector of which a part is exposed to an outside of the outer sleeve and the rest part is slidably coupled in the carrier so as to press the lancet and thus separate the lancet from the carrier.

* * * * *